United States Patent [19]

Jung et al.

[11] 3,970,679

[45] July 20, 1976

[54] PROCESS FOR THE PRODUCTION OF ORGANOTIN HALIDES IN SULPHONES AS REACTION MEDIUM

[75] Inventors: Hans Wolf Jung, Burstadt; Rudolf Maul, Bensheim; Hermann Wolfgang Wehner, Zwingenberg, all of Germany

[73] Assignee: Ciba-Geigy Corporation, Ardsley, N.Y.

[22] Filed: Oct. 10, 1974

[21] Appl. No.: 513,898

Related U.S. Application Data

[63] Continuation-in-part of Ser. No. 362,701, May 22, 1973, abandoned.

[30] Foreign Application Priority Data

May 25, 1972 Germany............................ 2225322

[52] U.S. Cl. ............................................. 260/429.7
[51] Int. Cl.$^2$........................................... C07F 7/22
[58] Field of Search ................................. 260/429.7

[56] References Cited

UNITED STATES PATENTS

| | | | |
|---|---|---|---|
| 3,414,595 | 12/1968 | Oakes | 260/429.7 |
| 3,415,857 | 12/1968 | Hoye | 260/429.7 |
| 3,449,451 | 6/1969 | Senatore | 260/429.7 |
| 3,454,610 | 7/1969 | Langer | 260/429.7 |
| 3,471,250 | 10/1969 | Langer | 260/429.7 |
| 3,745,183 | 7/1973 | Katsumura | 260/429.7 |

FOREIGN PATENTS OR APPLICATIONS

| | | |
|---|---|---|
| 2,108,966 | 9/1971 | Germany |
| 1,047,389 | 11/1966 | United Kingdom |

OTHER PUBLICATIONS

J. Organometallic Chem. V5, pp. 288–291 (1966).

*Primary Examiner*—Helen M. S. Sneed

[57] ABSTRACT

A process is described for the production of organotin halides from metallic tin and organic halides and in the presence of catalysts in sulphones as the reaction medium, whereby there are obtained, in addition to high yields, also high reaction rates.

9 Claims, No Drawings

PROCESS FOR THE PRODUCTION OF ORGANOTIN HALIDES IN SULPHONES AS REACTION MEDIUM

This application is a continuation-in-part application of our copending application Ser. No. 362,701, filed May 22, 1973 now abandoned.

The invention concerns a process for the production of organotin halides from metallic tin and organic halides, by which process are obtained, in addition to high yields, also high reaction rates.

Organotin halides are important intermediates for the production of stabilisers for chlorine-containing polymers. They are also used as catalysts and biocides. Various attempts to effect the direct synthesis of organotin halides from metallic tin and organic halides have already been described. Thus, for example, the reaction of gaseous methyl chloride with solid Cu-Sn-alloys at 300°(US Pat. No. 2,679,505), or with molten copper- and zinc-containing tin at 300°–400° (US Pat. No. 2,679,506), is known. Also $Mg_2Sn$-alloys have been used for the synthesis of organotin halides (DT Pat. No. 946,447). These processes in the case of alkylations with methyl chloride produce, however, yields of only around 50%, which are smaller still with the use of higher homologs. Better yields can be obtained only with the employment of bromides or iodides, which, however, are appreciably more expensive. There has therefore been no lack of efforts to improve by means of additional catalysts the yield from the reaction of organochlorides with metallic tin.

For instance, there are described in DT-OS No. 2,108,966 a large number of such catalysts, which consist, for example, of phosphanes, iodine and salts of secondary-group elements. These catalysts bring about considerable improvements compared with the results obtained with earlier processes, particularly in the case of the reaction of higher alkyl chlorides with tin. In long-duration tests, however, a disturbing precipitation of catalyst or reaction products on the surface of the tin becomes clearly noticeable, so that the rate of reaction diminishes in the course of time.

The present invention concerns a process for the production of organotin halides of the general formula $$R_n Sn Hal_{4-n}$$

wherein R represents a saturated, unsaturated, straight or branched alkyl group having 1 – 4 carbon atoms, Hal represents chlorine, bromine or iodine, and $n$ denotes 1, 2 or 3, by the reaction of metallic tin or tin alloys with organic halides of the formula $$R - Hal$$

wherein R and Hal have the above given meanings, in the presence of catalysts known per se as for instance those catalysts which consist of reaction products of A. one or more compounds of the general formula

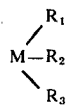

wherein
M is nitrogen or phosphorous, $R_1$, $R_2$, $R_3$ can be the same (except in the case of $R_1$, $R_2$, $R_3$ representing halogen) or different and represent hydrogen, halogen, saturated or unsaturated, linear or branched alkyl-, cycloalkyl-, aralkyl-, alkaryl- or aryl groups, optionally containing one or more functional groups, or represents the groups

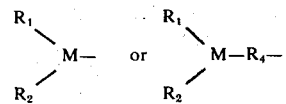

wherein $R_4$ is an alkylene group having from 1 to 8 carbon atoms and more of the groups $R_1$, $R_2$ and $R_3$ can form a ring or ring system, which can contain oxygen, including corresponding onium-compounds, and B. one or more compounds of the formula $$E_a X_b Y_c$$

wherein
E. is boron, silicon, titanium, vanadiu, chromium, manganese, iron, cobalt, nickel or copper,
X is a one- or more valent electronegative group,
Y is molecular ligand, which is fully or partially bonded in the coordination sphere of E,
a. is a whole number from 1 to 4 and, when E is titanium, vanadium, chromium, manganese, iron, cobalt, nickel or copper, a denotes 1 or 2,
b. is a whole number from 0 to 7 and when E is silicon or borine, denotes a whole number from 1 to 13,
c. is a whole number from 0 to 18 and, when E is borine or silicon, denotes a whole number from 0 to 11, in a molar ratio of 1 mol of compound B to 1 to 10 mol of Compound A and, preferably, in a molar ratio of 1 mol of compound B to 2 to 4 moles of Compound A, in which process the reaction is performed in the presence of at least one sulphone of the general formulae

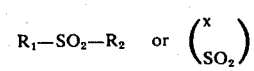

wherein $R_1$ and $R_2$, which can be identical or different, represent a saturated, unsaturated, straight or branched alkyl group having 1 – 4 carbon atoms, or a phenyl group optionally substituted by one or more methyl, halogen or nitro groups, and X represents a saturated or unsaturated, straight or branched hydrocarbon chain having 4 – 10 carbon atoms, optionally substituted by chlorine, hydroxyl, $(CH_3)_2N-$, acetoxy, sulpholanyloxy or alkoxy groups.

The use of sulphones unexpectedly effects a considerable improvement in yields compared with yields obtained with the usual solvents, even with those of similar polarity; a result which might indicate perhaps a complexing effect on the reaction products and/or on the catalyst, or a direct action of the sulphones in the reaction, for instance, in the form of an active intermediate. The result is all the more surprising since complexes from tin compounds and sulphones have not previously been known from the literature. The good dissolving power of the sulphones with respect to the organic starting and final products probably likewise has a useful effect on the reaction.

The particular advantage of the sulphones used according to the invention lies furthermore in the fact that with their application there is obtained an appreciable improvement of the space-time yield in the synthesis of important organotin halides. The high reaction rate makes possible the use even of the considerably cheaper commercial ingots in place of the expensive finely divided tin (powder, foil).

In the British Pat. No. 1,047,389 of the U.S. Pat. No. 3,414,595 and Canada Pat. No. 804,036, the organic sulphones, besides several other compounds, are claimed to have catalytic activity in the reaction of halogen compounds with tin or tin halides. The patent specification contains however no example of this. As is seen from Example 10 of our application, sulphones exhibit, at least in the case of the reaction of organic monohalides with tin, no catalytic activity.

Examples of organohalides usable according to the invention are methyl chloride, ethyl chloride, vinyl chloride, propyl chloride, i-propyl chloride, n- and i-butyl chloride. Naturally, it is also possible to use in the same manner the corresponding bromides or iodides. The process according to the invention renders possible, however, the use particularly of the cheap but less reactive chlorides.

Typical examples of the mentioned sulphones are tetramethylene sulphone (Sulfolan), butadiene sulphone (Sulfolen), 3-methylsulpholane, 2,4-dimethylsulpholane, 2,3-dimethylsulpholane, 3-chlorosulpholane, 2,3-dichlorosulpholane, 3-hydroxysulpholane, 3-chloro-4-hydroxysulpholane, 3-dimethylaminosulpholane, 3-acetoxysulpholane, di-3-sulpholanyl ether, methoxysulpholane, 3,4-dimethoxysulpholane, isopropoxysulpholane, tetrahydro-1-thiapyrane-1,1-dioxide, tetrahydro-tetramethyl-1-thiapyrane-1,1-dioxide, thiapane-1,1-dioxide, thiacane-1,1-dioxide, thianane-1,1-dioxide, dimethylsulphone, divinylsulphone, methyl-isopropyl-sulphone, ethyl-isopropyl-sulphone, di-n-butylsulphone, methyl-tert.butyl-sulphone, diphenylsulphone, phenyl-methyl-sulphone, tolylphenyl-sulphone, bis-(dichlorophenyl)-sulphone, 2,4,4',5-tetrachlorodiphenyl-sulphone, p-fluorophenyl-p-tolylsulphone, dinitrophenylsulphone, 4-fluoro-3,3'-dinitrodiphenylsulphone.

Cyclic sulphones having 4 carbon atoms in the ring are preferred, which also can be substituted by methyl groups or chlorine, particularly tetramethylene-sulphone.

The reaction temperature can be between 100° and the melting temperature of the tin; however, it is also possible to use tin melts up to about 300°, provided the employed sulphone is stable at the chosen temperature. Preferred temperatures are between about 150° and 220°, since secondary reactions can occur at higher temperatures.

The organohalide can be reacted at normal pressure or at elevated pressure. For reasons connected with the apparatus, the pressure should not however exceed 20 atmospheres. Pressures of 0 to 12 atmospheres are preferred; the reaction is preferably performed, in particular, under normal pressure.

The organotin halides can be isolated from the reaction mixture in a known manner. By virtue of the high boiling points of the employed sulphones, separation by distillation is particularly advantageous and, at the same time, yields products of high purity.

The distillation residue can be used without processing for further reactions. This offers the possibility of continuously adding tin and organohalide in a continuous process; to take off a portion of the reaction solution; to distill off from this the reaction product and return the residue to the process. Since the use of sulphones as solvent obviously maintains the surface of the tin reactive, it is this type of process in particular which is rendered possible.

EXAMPLE 1

100 Parts of tetramethylene sulphone, 5 parts of tin foil, 0.3 parts of anhydrous iron (III)-chloride, 0.1 part of iodine and 0.7 part of benzylamine are heated at 180° while stirring is maintained. Methyl chloride is passed through the reaction mixture until the whole of the tin has been reacted. The time required for the complete reaction of the tin is determined.

The process was carried out in an analogous manner in the case of the other systems given below, whereby normal solvents were used in place of tetramethylene sulphone.

| Reaction medium | Pressure (atm.) | Time for complete reaction of the tin, in hours |
| --- | --- | --- |
| tetramethylene sulphone | 1 | 6 |
| di-n-butyl ether | 4 | 35 |
| cyclohexylacetate | 1 | 70 |
| di-n-octyl ether | 1 | 39 |
| triethylene glycol dimethyl ether | 1 | 32 |
| diethylene glycol dimethyl ether | 1 | 46 |

EXAMPLE 2

120 Parts of tin shot, 300 parts of tetramethylene sulphone, 10 parts of iron(III)-chloride, 17 parts of iodine and 85 parts of tributylphosphane are heated together at 180°C. While stirring is maintained, methyl chloride is passed through the mixture. The whole of the tin has been reacted after 4 hours. A further 120 parts of tin shot are added and the procedure carried out as above. When this amount of tin has been consumed, a further amount of tin shot is added. The reaction is terminated after 50 hours. 960 Parts of tin have been reacted. From time to time the tinorganic reaction product is distilled off in vacuo from the reaction solution. The distillate (in all 1570 parts) contains 93% of dimethyltin dichloride, 5% of monomethyltin trichloride and 2% of trimethyltin chloride.

EXAMPLE 3

400 Parts of tin granulate, 400 parts of tetramethylene sulphone and 10 parts of iodine are heated together at 175°– 185° while stirring is maintained. Methyl chloride is passed through the reaction mixture. The occurring tinorganic reaction products are distilled off in vacuo from time to time. The whole of the tin has been reacted after 32 hours.

EXAMPLE 4

400 Parts of tin granulate, 400 parts of tetramethylene sulphone, 10 parts of iodine and 8 parts of tributylphosphane are heated together while stirring is maintained. Methy chloride is passed through the reaction mixture and the reaction product separated by distillation in vacuo. The whole of the tin has been reacted after 29 hours.

EXAMPLE 5

100 Parts of 3-methylsulpholane, 5 parts of tin foil, 0.1 part of iodine, 1 part of tributylphosphane and 0.1 part of iron(III)-chloride are heated together at 180°. Methyl chloride is passed through the reaction mixture at this temperature while stirring is maintained. The whole of the tin has been reacted after 6 hours.

EXAMPLE 6

100 Parts of dimethylsulphone, 5 parts of tin foil, 0.2 part of orthoboric acid, 1.4 parts of n-octylamine and 0.2 part of iodine are heated together at 180°. Methyl chloride is passed through the reaction mixture. The whole of the tin has been reacted to methyltin chlorides after 8 hours.

EXAMPLE 7

100 Parts of 2,3-dichlorosulpholane, 5 parts of tin foil, 0.5 part of cobalt (II)-chloride and 2 parts of di-n-octylphosphane are heated together, with stirring, at 190°. Ethyl chloride is passed through the reaction mixture. The whole of the tin has been reacted after 7 hours.

EXAMPLE 8

100 Parts of butadienesulphone, 5 parts of tin foil, 0.4 part of manganese(II)-sulphide, 3 parts of tri-n-butylphosphane and 0.2 part of iodine are heated together with 10 parts of n-butyl chloride in a pressure vessel, with stirring, for 10 hours at 180°. 4.1 Parts of tin have been reacted.

EXAMPLE 9

100 Parts of di-n-butylsulphone, 5 parts of tin, 0.3 part of nickel(II)-sulphide, 2.5 parts of tri-n-butylphosphane and 0.2 part of iodine are heated together at 200°. Methyl chloride is passed through the mixture at this temperature while stirring is maintained. The tin has been quantitatively reacted to methyltin chlorides within 11 hours.

EXAMPLE 10

(comparative example)

100 g of dichlorobenzene, 7.6 g of di-n-butylsulphone and 28.6 g of tin shot are heated, with stirring, until the solvent boils. Methyl chloride is passed through the reaction mixture. The whole of the tin remains unchanged after a reaction duration of 20 hours.

What is claimed is:

1. In the process for the production of organotin halides of the formula $$R_nSn\ Hal_{4-n}$$

wherein R represents a saturated, unsaturated straight or branched alkyl group having 1 – 4 carbon atoms, Hal represents chlorine, bromine or iodine, and $n$ denotes 1, 2 or 3, by the reaction of metallic tin or tin alloys with organic halides of the formula $$R - Hal$$

wherein R and Hal have the above given meanings, at 100°–300°C, at a pressure of 0 – 20 atmospheres and in the presence of a catalyst system, consisting of the reaction products of A. one or more compounds of the general formula

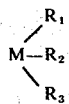

wherein
M is nitrogen or phosphorous,
$R_1$, $R_2$, $R_3$ can be equal (excepted in the case of $R_1$, $R_2$,
$R_3$ representing halogen) or different and represent hydrogen, halogen, saturated or unsaturated, linear or branched alkyl-, cycloalkyl-, aralkyl-, alkaryl- or aryl groups, optionally containing one or more functional groups, or represents the groups

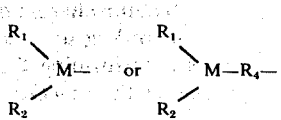

wherein $R_4$ is an alkylene group having from 1 to 8 carbon atoms and more of the groups $R_1$, $R_2$ and $R_3$ can form a ring or ring system, which can contain oxygen, including corresponding onium-compounds, and B. one or more compounds of the formula $$E_aX_bY_c$$

wherein
E is borine, silicon, titanium, vanadium, chromium, manganese, iron, cobalt, nickel or copper,
X is a one- or more valent electronegative group,
Y is molecular ligand, which is fully or partially bonded in the coordination sphere of E,
$a$ is a whole number from 1 to 4 and, when E is titanium, vanadium, chromium, manganese, iron, cobalt, nickel or copper, $a$ denotes 1 or 2,
$b$ is a whole number from 0 to 7 and when E is silicon or borine, denotes a whole number from 1 to 13,
$c$ is a whole number from 0 to 18 and, when E is borine or silicon, denotes a whole number from 0 to 11,
in a molar ratio of 1 mol of compound B to 1 to 10 mol of compound A, the improvement which comprises performing said reaction in at least one sulphone of the formulae $$R_1-SO_2-R_2\ \ or\ X\ \ SO_2$$

wherein $R_1$ and $R_2$ represent identical or different, saturated or unsaturated, straight or branched alkyl groups having 1 - 4 carbon atoms, or phenyl or phenyl substituted by one or more methyl, halogen or nitro groups, and X represents a saturated or unsaturated, straight or branched hydrocarbon chain having 4 – 10 carbon atoms or such a hydrocarbon chain which is substituted by chlorine, hydroxy, $(CH_3)_2N$-, acetoxy, sulpholanyloxy or alkoxy groups, as reaction medium.

2. A process according to claim 1, wherein the reaction is performed at 150°– 220°C and at a pressure of 0 – 12 atmospheres.

3. A process according to claim 1 wherein said sulphone is a cyclic sulphone having 4 carbon atoms in the ring or such cyclic sulphone substituted by methyl groups or by chlorine.

4. In the process for the production of organotin halides of the formula

wherein R represents a saturated, unsaturated, straight or branched alkyl group having 1 – 4 carbon atoms, Hal represents chlorine, bromine or iodine, and $n$ denotes 1, 2 or 3,
by the reaction of metallic tin or tin alloys with organic halides of the formula

wherein R and Hal have the above given meanings, at 100°- 300°C, at a pressure of 0 – 20 atmospheres and in the presence of catalyst system according to claim 1, the improvement which comprises performing the reaction in tetramethylene sulphone as the reaction medium.

5. A process according to claim 4 wherein the reaction is that of methyl chloride with metallic tin.

6. A process according to claim 1, characterized in that additionally 0.01 to 1, preferably 0.05 to 0.5 mol iodine or iodine compounds are used pro mol of tin in the catalyst system.

7. A process according to claim 1, wherein the molar ratio is 1 mol of B) to 2 to 4 moles of A.

8. A process according to claim 1 which comprises the presence of iron(III) chloride as component B) of the catalyst system.

9. A process according to claim 1 in which the catalyst consists essentially of
a. anhydrous iron(III)-chloride, benzylamine and iodine,
b. iron(III)-chloride, tributylphosphane and iodine,
c. iodine,
d. tributylphosphane and iodine,
e. orthoboric acid, n-octylamine and iodine
f. cobalt(II)-chloride and di-n-octylphosphane,
g. manganese(II)-sulfide, tri-ni-butylphosphane tri-n-butylphosphane iodine, or
h. nickel(II)-sulfide, tri-n-butylphosphane and iodine.

* * * * *